(12) United States Patent
Ayala et al.

(10) Patent No.: US 8,252,308 B2
(45) Date of Patent: Aug. 28, 2012

(54) FEMININE ANTI-ITCH GEL

(75) Inventors: Nelson Ayala, Lynchburg, VA (US); Michael L. Caswell, Lynchburg, VA (US)

(73) Assignee: C.B. Fleet Company Inc., Lynchburg, VA (US)

( * ) Notice: Subject to any disclaimer, the term of this patent is extended or adjusted under 35 U.S.C. 154(b) by 889 days.

(21) Appl. No.: 11/814,972

(22) PCT Filed: Jan. 27, 2005

(86) PCT No.: PCT/US2005/002946
§ 371 (c)(1),
(2), (4) Date: May 12, 2008

(87) PCT Pub. No.: WO2006/080924
PCT Pub. Date: Aug. 3, 2006

(65) Prior Publication Data
US 2009/0111814 A1    Apr. 30, 2009

(51) Int. Cl.
*A61K 31/535* (2006.01)
*A61K 47/00* (2006.01)
*A61F 6/06* (2006.01)

(52) U.S. Cl. ............... 424/430; 514/174; 514/232.2; 514/816; 514/944; 514/947; 514/238.2; 514/239.2; 514/887

(58) Field of Classification Search ............ 514/159, 514/239.2, 536, 312, 734, 944, 975, 174, 514/232.2, 816, 947, 887; 424/430
See application file for complete search history.

(56) References Cited

U.S. PATENT DOCUMENTS

| 3,965,908 | A | * | 6/1976 | Posthuma et al. ............ 606/108 |
|---|---|---|---|---|
| 4,673,570 | A | | 6/1987 | Soldati |
| 4,788,060 | A | | 11/1988 | Endicott et al. |
| 4,895,727 | A | | 1/1990 | Allen |
| 5,137,718 | A | | 8/1992 | Gillespie |
| 5,216,033 | A | | 6/1993 | Pereira et al. |
| 5,549,887 | A | | 8/1996 | Galleguillos et al. |
| 5,929,338 | A | | 7/1999 | Frankel et al. |
| 6,007,799 | A | * | 12/1999 | Lee et al. ............ 424/65 |
| 6,093,414 | A | | 7/2000 | Capelli |
| 6,156,323 | A | | 12/2000 | Verdicchio et al. |
| 6,159,485 | A | | 12/2000 | Yu et al. |
| 6,200,964 | B1 | | 3/2001 | Singleton et al. |
| 6,258,374 | B1 | | 7/2001 | Friess et al. |
| 6,384,023 | B2 | * | 5/2002 | Singleton et al. ............ 514/159 |
| 6,391,869 | B1 | | 5/2002 | Parks et al. |
| 6,395,736 | B1 | | 5/2002 | Parks et al. |

(Continued)

FOREIGN PATENT DOCUMENTS

WO  03/053180  7/2003

(Continued)

OTHER PUBLICATIONS http://physics.info/viscosity/ accessed May 19, 2010.*

(Continued)

*Primary Examiner* — Savitha Rao
(74) *Attorney, Agent, or Firm* — Evan Law Group LLC

(57) ABSTRACT

The present invention provides a substantially clear gel designed to reduce itching discomfort when applied to the vulvar tissue. The gel includes at least one anesthetic, protectant, emulsifier, and pH modifier, such as a base. The gel has a pH adapted to vulvar use and may be applied to the vulvar tissues.

32 Claims, 2 Drawing Sheets

U.S. PATENT DOCUMENTS

| | | | |
|---|---|---|---|
| 6,420,425 B1 | 7/2002 | Melman | |
| 6,432,891 B1 | 8/2002 | O'Connor | |
| 6,444,647 B1 | 9/2002 | Robinson et al. | |
| 6,479,058 B1 | 11/2002 | McCadden | |
| 6,492,326 B1 | 12/2002 | Robinson et al. | |
| 6,495,097 B1 | 12/2002 | Streit et al. | |
| 6,524,593 B1 | 2/2003 | Yu et al. | |
| 6,524,623 B1 | 2/2003 | Hodosh | |
| 6,555,508 B1 | 4/2003 | Paul et al. | |
| 6,627,632 B2 | 9/2003 | Parks et al. | |
| 6,653,352 B2 | 11/2003 | Barr et al. | |
| 6,656,168 B2 | 12/2003 | Braverman et al. | |
| 6,656,928 B1 | 12/2003 | McCadden | |
| 6,664,254 B1 | 12/2003 | Rogozinski | |
| 6,794,343 B2 | 9/2004 | Paul et al. | |
| 6,818,204 B2 | 11/2004 | Lapidus | |
| 6,824,786 B2 | 11/2004 | Yu et al. | |
| 7,488,474 B2 * | 2/2009 | Sakaguchi et al. | 424/93.71 |
| 2002/0034455 A1 * | 3/2002 | Lapidus | 422/37 |
| 2003/0050247 A1 | 3/2003 | Kuhner et al. | |
| 2004/0204366 A1 * | 10/2004 | Pasternak et al. | 514/17 |
| 2006/0147504 A1 * | 7/2006 | Corry et al. | 424/443 |

FOREIGN PATENT DOCUMENTS

| | | |
|---|---|---|
| WO | WO 2006/073467 | 7/2006 |
| WO | WO 2006/080924 | 8/2006 |

OTHER PUBLICATIONS

Comforth article, Aug. 4, 2004, Downloaded from the internet on May 26, 2011, URL: http://web.archive.org/web/20040804080250/http://womenshealth.about.com/cs/pregnancy/a/vagitchpregnanc.htm.*

Abstract of: Currie, J. L., et al., "Potential for an external vaginal antiitch cream containing benzocaine to cause methemoglobinemia in healthy women"., American Journal of Obstetrics and Gynecology, vol. 176, No. 5, pp. 1006-1008, (1997).

Allison, A-M., et al.,"Fiery and frosty foods pose challenges in sensory evaluation"., Food Technology, vol. 58, No. 5, pp. 32-37, (2004).

Care Chemicals, A-Z Product Catalog, http://www.fitzchem.com/pdf/A-Z-guide-9-04.pdf, pp. 1-30, (2004).

International Search Report dated Oct. 11, 2005 for corresponding PCT application No. PCT/US2005/017687.

Product list for Pachem Distribution Incorporated, pp. 1-4 printed from http://pachemdistribution.com/pages/prod.html, Dec. 29, 2004, Complete product list additional pp. 1-5.

Product description for Fleet Pain-Relief Pre-Moistened Anorectal Pads, http://www.drugstore.com/products.asp?pid+27194, pp. 1-3, (2006).

"Skin protectant drug products for over-the-counter human use; Final monograph"., Department of Health and Human Services, Food and Drug Administration, Federal Register, vol. 68, No. 107, pp. 33362-33381, (2003).

Turbidity, Wikipedia free encyclopedia, http://en.wikipedia.org/wiki/Turbidity, pp. 1-2, Nov. 9, 2005.

Belle-Aire Fragrances Inc., ORDENONE™ Eliminates Malodors Forever, 2 pages, (2004).

Dow Corning® 5225C Formulation Aid Product Information, 2 pages, (2001).

Dow Corning® 3225C Formulation Aid Material Safety Data Sheet, 9 pages, (2003).

Dow Corning® 3225C Formulation Aid Product Information, Personal Care, 2 pages, (2004).

Dow Corning® 5225C Formulation Aid Material Safety Data Sheet, 7 pages, (2003).

Dow Corning® 345 Fluid, Product Information, Personal Care, 4 pages, (1998).

Dow Corning® 345 Fluid, Material Safety Data Sheet, 8 pages, (2003).

* cited by examiner

FEMININE ANTI-ITCH GEL

BACKGROUND

Itching and the associated discomfort that accompanies skin irritation are common annoyances. The discomfort caused by itching is especially problematic when experienced at vulvar tissues of the body. Vulvar tissues form the surfaces of the female genitalia, but do not extend into the vaginal canal.

Itching of the vulvar tissues may be especially uncomfortable. Furthermore, these tissues are quite sensitive and may be irritated by products intended to relieve the itching discomfort associated with skin and other tissue types. Conventional preparations for treating vulvar itching, such as Vagisil® cream, include benzocaine and are white in color. While an effective topical anesthetic, benzocaine can induce an undesirable sensitivity in some users with regular use. Furthermore, creams are opaque white and are not transparent to the user after application. Creams also have an unpleasant "greasy" feel and are not easily washed from under the nails after application. Other conventional preparations, such as the foams described in U.S. Pat. No. 6,818,204, are primarily for cleansing and include little protectant.

SUMMARY

In one aspect, the invention provides an anti-itch gel that includes a water-soluble anesthetic, a pH modifier, from 5 to 60% by weight of a protectant, and a water-in-oil emulsifier, where the gel has a turbidity of less than 100 nephelometric turbidity units. A method of treating vulvar discomfort with this gel also is provided.

In another aspect, the invention provides an anti-itch gel that includes from 20 to 60% by weight water, a water-soluble salt of pramoxine, and a water-in-oil emulsifier comprising one or more silicones.

In yet another aspect of the invention, a method for forming an anti-itch gel for treating the itching associated with the vulvar tissues is provided that includes combining a water phase with an oil phase after matching the refractive indices of the water and oil phases to within 0.0004 to 0.0017 to provide the gel a turbidity of less than 100 nephelometric turbidity units; where the water phase includes water, a water-soluble anesthetic, and a protectant; and the oil phase includes a water-in-oil emulsifier.

The following definitions are included to provide a clear and consistent understanding of the specification and claims.

The terms "gel" or "emulsion" are used interchangeably to denote a colloidal suspension including a water phase dispersed in an oil phase having a viscosity of from 5 to 50 thousand or preferably from 10 to 30 thousand centipoises, when measured at 25° C. on a Brookfield Viscometer, available from Brookfield Engineering Laboratories, Middleboro, Mass.

The term "emulsifier" means a substance that reduces the coagulation of dispersed colloidal particles to assist in maintaining the average diameter of the dispersed particles. Water-in-oil emulsifiers are not substantially soluble in water and may provide an external coating to water droplets.

The term "surfactant" means a surface-active substance, such as a detergent or soap, which lowers the surface tension of water. As used herein, surfactants are water-soluble and may be diluted by water.

The term "emollient" means a liquid that has a moisturizing effect when applied to body tissues exposed to the atmosphere.

The terms "soluble" or "solubilized" mean a solid solvated in a liquid to provide a solution, where a solution, unlike a dispersion, suspension, or mixture, lacks an identifiable interface between the solubilized solid and the solvent. Thus, in solutions, the solubilized solid is in direct contact with the solvent, while in colloidal suspensions only the surface of the colloidal particles are in direct contact with the liquid.

The term "particle" may refer to a solid or a liquid droplet suspended in a liquid.

The average diameter of an individual particle is the average of a plurality of diameter measurements for the individual particle. For example, if an individual particle has measured diameters of 6, 8, and 10 microns, the average diameter of the individual particle is 8 microns. The diameters of individual particles may be determined by observation with a compound light microscope equipped with image processing software, such as the Image Pro Express Version 4.5 software package available from Media Cybernetics, Silver Spring, Md.

The "average particle diameter" of a gel is the average of the average diameters of the individual colloidal particles contained in the gel. For example, if a gel includes particles having average diameters of 2, 6, 6, and 10 microns, the average particle diameter of the gel is 6 microns

DETAILED DESCRIPTION

Conventional creams for treating the discomfort caused by vulvar itching are opaque white and include benzocaine as an anesthetic. The present invention makes use of the discovery that consumers prefer a substantially clear gel over an opaque white cream to treat vulvar itching. Reasons for this consumer preference include the fact that the gel is less messy and that the gel does not leave a residue after application.

By appropriately matching the refractive indices of water and oil phases before combination, a substantially clear gel may be provided. In another aspect, by replacing benzocaine, an anesthetic that is water insoluble, with a water-soluble anesthetic, a substantially clear anesthetic gel may be formed. The pH of the substantially clear gel may be selected to provide a neutral form of the anesthetic for enhanced availability to the vulvar tissues, while keeping the anesthetic substantially solubilized in the water phase of the gel. Furthermore, when pramoxine hydrochloride is used as the water-soluble anesthetic, an additional benefit may be that the undesirable sensitivity that some users develop from using benzocaine based products is avoided.

The substantially clear gel of the present invention may treat the discomfort caused by vulvar itching. This itching may result from abrasion of the vulvar tissues and/or from other causes, including minor bacterial and/or fungal infection. By "substantially clear" it is meant that when the ingredients of the gel are combined, the gel has a turbidity at 24° C. of less than 100 Nephelometric Turbidity Units (NTU) when measured with a Micro100 turbidity instrument available from HF Scientific, Inc., Fort Myers, Fla. In a preferred aspect, a substantially clear gel has a turbidity of less than 50 NTU, less than 40 NTU, or more preferably less than 35 NTU. At present, an especially preferred turbidity for substantially clear gels is from 25 to 35 NTU.

Figure 1:
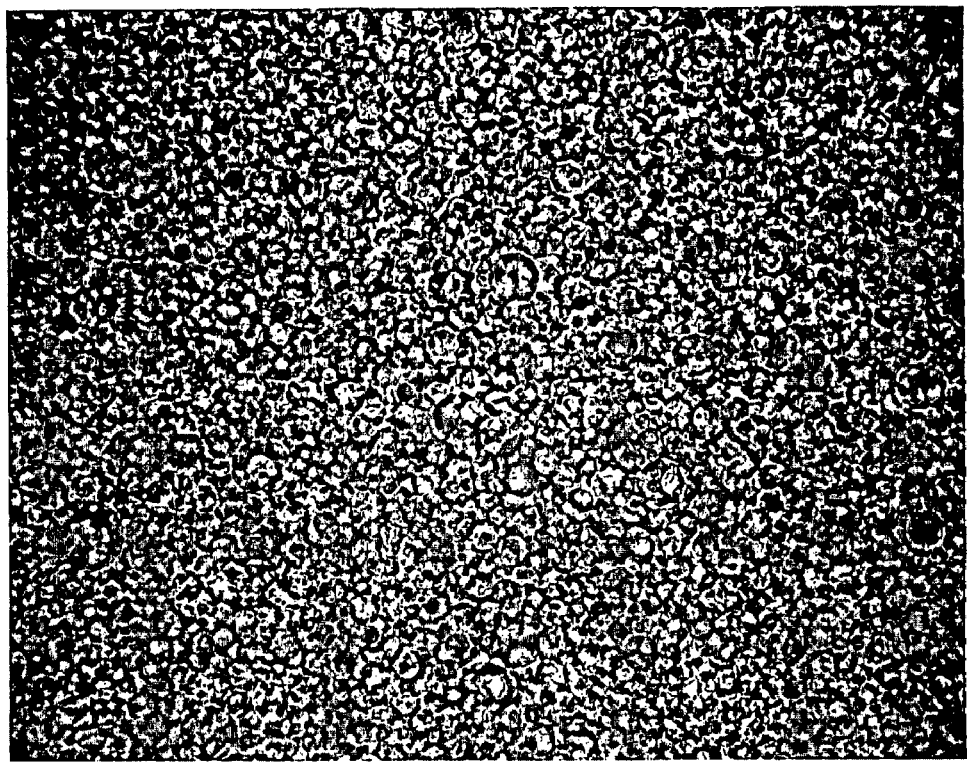
FIG. 1 is an image of a water-in-oil emulsion in accordance with the present invention having dispersed colloidal particles with average diameters from approximately 2 to 10 microns and an average particle diameter of about 5 microns.

FIG. 1 is an image of a substantially clear gel in accordance with the present invention having dispersed colloidal particles with average diameters from 2 to 10 microns and an average particle diameter of about 5 microns. Both the water phase that forms the colloid particles and the oil phase that surrounds the particles of the gel are substantially clear. It is presently believed that the depicted colloid particles have an interior core of water that includes the water soluble ingredients and a thin outer coating, in this aspect less than 500 nm thick, of an oil phase.

Figure 2:
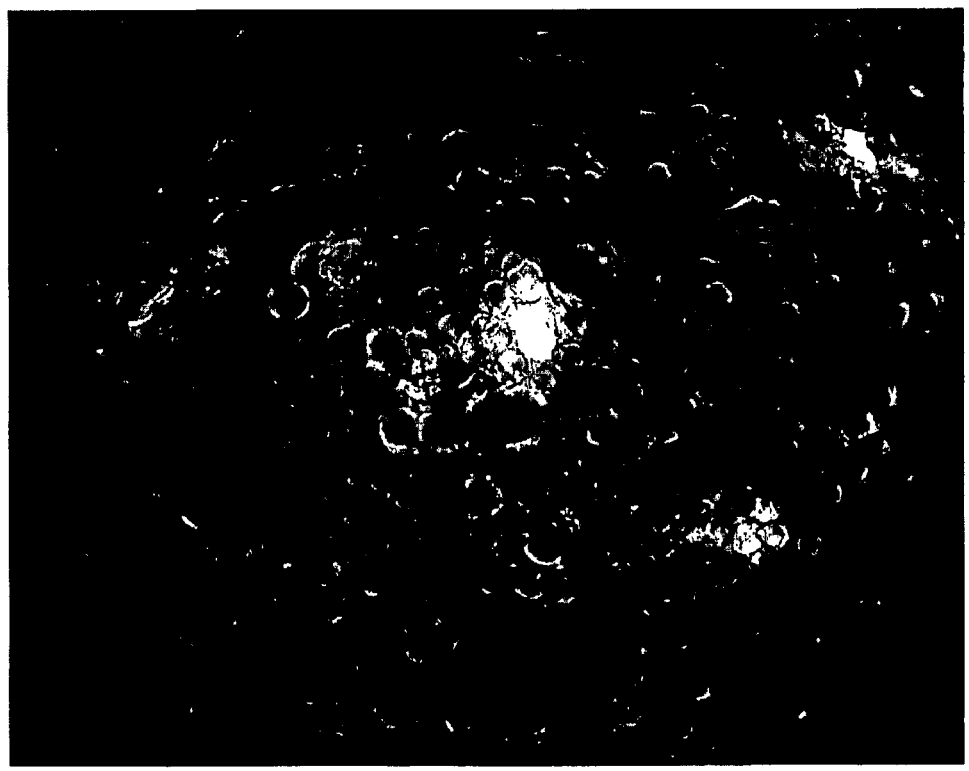
FIG. 2 is an image of the conventional oil-in-water emulsion of Vagisil® cream having an average particle diameter of about 15 microns.

In contrast to FIG. 1, FIG. 2 is an image of the conventional oil-in-water emulsion of Vagisil® cream. Unlike the present water-in-oil emulsion, when the refractive indexes of the two component mixtures of an oil-in-water emulsion are matched before combination, a substantially clear product does not generally result unless the colloidal particles have an average particle diameter of less than 400 nm, the shortest wavelength of visible light. The colloidal particles in FIG. 2 have average diameters from about 10 to 20 microns and an average particle diameter of about 15 microns. Thus, these colloidal particles are too large to provide a substantially clear product.

Furthermore, the conventional cream of FIG. 2 includes solid benzocaine particles dispersed in a water phase that may be seen as the solid white areas. These solid benzocaine particles have average diameters from approximately 20 to 30 microns and are thus large enough to diffract visible light and provide a white color to the cream.

The gel of the present invention may include one or more solvents, emulsifiers, emollients, bases, preservatives, anesthetics, protectants, clarity modifiers, fragrances, and odor neutralizing agents. Preferably, the solvent includes water, with the gel preferably including from 20 to 60% or from 30 to 50% water, with about 37 to 42% water being more preferred. Unless stated otherwise, all percentages of ingredients in the gel are stated on a weight/weight (w/w) basis.

A substantially clear gel may be prepared by combining two mixtures having matched refractive indices (RI). The first mixture may include the solvent, pH modifier, preservative, anesthetic, and protectant, while the second mixture may contain the emulsifier and optionally the emollient. In one aspect, the first mixture is water-based to provide a water phase while the second mixture is oil based to provide an oil phase. In a preferred aspect, the emulsifier and emollient present in the oil phase are silicone based oils.

Before combination, the refractive index of first mixture may be matched to the refractive index of the second mixture. In a preferred aspect, additional protectant, e.g. glycerin, may be added to the first mixture to raise the refractive index to approximate that of the second mixture. Similarly, additional solvent, e.g. water, may be added to the first mixture to lower the refractive index to approximate that of the second mixture. For example, if the refractive index of the second mixture including the emulsifier is 1.3975±1%, and the refractive index of the first mixture is 1.3333, then additional glycerin may be added to the first mixture to raise the 1.3333 value to approximate the 1.3975 value.

If the matching of the refractive indices of the first and second mixtures results in a difference in the refractive indices between the two mixtures of about 0.0016, a turbidity of about 100 NTU may be obtained. Similarly, differences in the refractive indices between the two mixtures of at most 0.0013, 0.0010, or 0.0005 may result in gel turbidities of less than 50, 30, and 15 NTU, respectively. Thus, the smaller the difference in the refractive indices between the two mixtures before combination, the clearer the resulting gel may be. Presently, preferable differences in the refractive indices for the first and second mixtures before combination are from 0.0004 to 0.0017, or more preferably from 0.0008 to 0.0013.

Upon combination, the average particle diameter of the colloidal particles present in the gel is preferably from 1 to 50 microns or from 2 to 30 microns. In a more preferred aspect, the colloidal particles have an average particle diameter of from 2 to 15 or from 2 to 8 microns. However, after combination the colloidal particles may coalesce, thus increasing the average particle diameter of the gel. As the average particle diameter of the gel increases, the viscosity of the gel decreases. This decrease in gel viscosity may result in the gel loosing a substantial portion of its thickness and also may result in a more lotion-like product.

A water-in-oil emulsifier may be chosen to maintain the average particle diameter of the colloidal particles present in the gel after combination of the water and oil phases. Through the use of one or more water-in-oil emulsifiers, the viscosity of the gel may be substantially retained after packaging and storage; thereby providing a gel having the desired thickness over an enhanced shelf-life. Without the emulsifier, the colloidal particles that form the gel may coalesce into larger particles over time and form a lotion.

Any water-in-oil emulsifier that is compatible with the other gel components and the vulvar tissues and that provides the desired clarity to the gel may be used. In one aspect, silicone-based emulsifiers are preferred. In another aspect, a dimethicone copolyol based emulsifier may be preferred. In one aspect, the composition may include from 5 to 20% or from 8 to 16% of the emulsifier. In a preferred aspect, the composition may include from 10 to 14% of the emulsifier, with about 10 to 12% being more preferred.

Examples of more preferred dimethicone copolyol based emulsifiers include Dow Corning 3225C, Dow Corning 5225C, or mixtures thereof. Dow Corning 3225C includes from 15 to 30% cyclopentasiloxane, greater than 60% cyclotetrasiloxane, and about 10% of a non-volatile PEG/PPG-18/18 dimethicone component. Dow Corning 5225C includes about 90% cyclopentasiloxane and about 10% of the non-volatile PEG/PPG-18/18 dimethicone component.

Unlike the anesthetic cleansing foam described in U.S. Pat. No. 6,818,204, which includes about 21% substantially water-soluble surfactants to provide an effective cleanser, the anti-itch gel of the present invention preferably includes less than 10% and more preferably less than 5% of a water-soluble surfactant. In an embodiment especially preferred at present, the gel includes substantially no water-soluble surfactant. Thus, the composition of the present invention lacks a sufficient amount of surfactants to serve as an effective cleanser.

While the anti-itch gel of the present invention may be enclosed in a tube, bottle, envelope, and the like to maintain effectiveness, a preservative may be added to increase shelf-life. In one aspect, the preservative may include methylisothiazalinone (NEOLONE™), sodium benzoate, disodium EDTA, cetyl pyridinium chloride (CPC), benzalkonium chloride, 3-(p-chlorphenoxy)-1,2-propanediol(chlorphenesin), or combinations thereof. However, any preservative that is compatible with the other gel components and vulvar tissue may be used. The gel may include from 0.01 to 1% or from 0.05 to 0.2% of the preservative, in a preferred aspect, from 0.08 to 0.12%.

To aid in reducing itching, the gel may include one or more emollients. The emollient also may assist in reducing how greasy the gel feels to the user. In a related aspect, the emollient may decrease the viscosity of the gel that would otherwise result. Thus, the more of a protectant, such as glycerin, incorporated into the gel, the more preferable it may become to include one or more emollients.

In one aspect, the emollient may include a silicone-based liquid that volatilizes when applied to the skin. In a preferred aspect, the emollient may include a cyclomethicone, such as Dow Corning 345 Fluid; Dow Corning 245 Fluid, Shin Etsu KF994, Shin Etsu 9945, General Electric SF 1204, General Electric SF 1202, Wacker Silicones F-222, Union Carbide Volatile Silicone 7158, Goldschmidt Abil B 8839, or mixtures thereof. In one aspect, the gel may include from 2 to 20% or from 5 to 16% of the emollient. In a preferred aspect, the composition may include from 6 to 10% of the emollient, with about 8% being more preferred.

Additionally, the gel includes one or more anesthetics and protectants as active ingredients. The anesthetic may numb the vulvar tissues, thereby reducing discomfort. Preferable anesthetics form water-soluble salts that may be solubilized in water to provide substantially clear solutions. In one aspect, the anesthetic may include pramoxine, lidocaine, dibucaine, tetracaine, resorcinol, derivatives thereof, salts thereof, or mixtures thereof. The concentration of anesthetic included in the composition may depend on the numbing ability of the anesthetic. For example, from 5 to 20% of an anesthetic, such as benzocaine, may be required to provide a similar anesthetic effect to from 0.5 to 2% of pramoxine.

Pramoxine and its water-soluble salts may be preferred as an anesthetic because unlike some anesthetics, including benzocaine, pramoxine has a reduced tendency to sensitize the vulvar tissues. Pramoxine also may be preferred because it may be formulated as a water-soluble salt that may form a substantially clear solution in water. The ability of pramoxine salts to solubilize in water directly contrasts with many anesthetics, including benzocaine, which forms a cloudy, opaque solution attributable to water insolubility. In a more preferred aspect, the anesthetic includes from 0.5 to 2%, preferably from 0.8 to 1.5%, and more preferably from 0.9 to 1.1% of the hydrochloride salt of pramoxine.

The composition may include a pH modifier to adjust the pH of the gel. The pH modifier may be selected to provide a pH to the gel that reduces the chance that additional irritation of the vulvar tissues will result. The pH modifier also may be selected to impart a pH to the gel that provides some inhibition to undesirable bacterial and/or fungal growth. In one aspect the pH modifier may include basic hydroxide salts, such as sodium or potassium hydroxide. The gel may include from 0.005 to 0.08% or from 0.02 to 0.06% of pH modifier, in a preferred aspect, from 0.4 to 0.5%.

In a preferred aspect, the pH modifier and the quantity of the pH modifier are selected to provide a pH to the composition of from 4 to 7, from 4.5 to 6.5, or more preferably from 5 to 5.3 when pramoxine serves as an anesthetic. In one aspect, the preferred pH for the gel is a pH value where the anesthetic is substantially present in its neutral state. For example, the hydrochloride salt of pramoxine has an acidic pH in water of about 4. However, at about pH 5 the pramoxine salt deprotonates to a neutral form that may provide increased transfer of the anesthetic into the vulvar tissues. Thus, a sufficient quantity of a base may be added to the gel as a pH modifier to provide the anesthetic in a substantially neutral form. However, at an upper pH value, such as about 5.2 for pramoxine, the anesthetic may precipitate out of the water phase, thus reducing the clarity of the gel. Thus, in a more preferred aspect, the pH modifier is chosen to provide a pH to the gel at which the majority of the anesthetic is present in its neutral state while remaining substantially solubilized.

By coating the vulvar tissue, the protectant may provide an additional reduction in itching discomfort and protect the tissue from further irritation. In this manner, minor abrasions may be protected from further abrasion by the surrounding tissues and clothing. The abrasions also may be partially isolated from the atmosphere, thus assisting in keeping the tissue moist and reducing the likelihood of fungal or bacterial attack. Preferable protectants are compatible with the other components of the gel and with vulvar use. More preferable protectants have the desired compatibility and also provide a substantially clear gel when combined in the gel.

Suitable protectants and preferred concentrations for protectant use in the gel may be found in 21 C.F.R. §§ 310, 347, and 352 (Fed. Reg., Vol. 68, No. 107, Jun. 4, 2003, pp. 33362-81), for example. More preferred protectants and the weight percentage required for the protectants to qualify as a skin protectant under FDA guidelines are found in 21 C.F.R §247.10. Thus, in one aspect, more preferred protectants for use in the present gel include from 20 to 45% glycerin, from 1 to 30% dimethicone, or mixtures thereof. The gel may include from 5 to 60% of the protectant, preferably from 30 to 50%, and more preferably from 20 to 40%. In an aspect especially preferred at present, the gel includes from 37 to 43% of the protectant.

At present, glycerin is an especially preferred protectant due to its ability to increase the refractive index of the water phase while remaining solubilized in the water. However, the amount of the protectant may be reduced in relation to the amount required to increase the refractive index of the water phase to approximate that of the oil phase by including a clarity modifier in the gel. For example, if it is desirable to reduce the amount of glycerin in the gel from the amount required to approximate the refractive index of the oil phase in the water phase, a clarity modifier may be added. Preferable clarity modifiers include propylene glycol, sorbitol, hexane diol, or combinations thereof. The preferable amount of clarity modifier to include in the gel may depend on multiple factors, including the amount of protectant present in the gel, the refractive index desired for the water phase, or a combination thereof.

In comparison to foaming compositions having a significant cleansing function, such as those described in U.S. Pat. No. 6,818,204, the present gel includes a greater protectant concentration. Furthermore, the protectant concentration of the present gel is incompatible with the formation of stable foams. Thus, the protectant concentration of the present anti-itch gel may provide better protection to the vulvar tissues in relation to foam-based cleaning products.

The gels of the present invention also may include one or more odor modifiers that may include fragrances and/or odor neutralizing agents. Suitable fragrances may be any fragrance composition known to those of skill in the art that is compatible with the other gel components and vulvar use. In a preferred aspect, the fragrance and/or odor neutralizing agents also are compatible with the formation of a substantially clear gel. Examples of fragrances include light florals and the like.

Suitable odor neutralizing agents may include any composition that traps odor causing compounds, such as amines, sulfides, mercaptans, and the like. One such odor neutralizing agent is the water-based, semi-rigid, concave molecular structures sold as Ordenone® by Belle-Aire Fragrances, Inc., Mundelein, Ill. Examples of various odor modifiers that may be useful in the present gel may be found in U.S. Pat. Nos. 6,432,891; 6,495,097; and 6,664,254, the relevant portions of which are incorporated herein by reference.

The following examples are provided to illustrate one or more preferred embodiments of the invention. Numerous variations can be made to the following examples that lie within the scope of the invention.

EXAMPLES

Example 1

An anti-itch gel including the ingredients listed below in Table 1 was prepared.

TABLE 1

| Ingredient | Weight Percent (w/w) |
|---|---|
| Pramoxine HCl - USP | 1 |
| Glycerin 99% - USP | 38.7 |
| Dow Corning 3225C | 12 |
| Dow Corning 345 | 8 |
| 20% KOH | 0.04 |
| NEOLONE ™ | 0.1 |
| Water | 40.16 |

Example 2

An anti-itch gel including the ingredients listed below in Table 2 was prepared.

TABLE 2

| Ingredient | Weight Percent (w/w) |
|---|---|
| Pramoxine HCl - USP | 1 |
| Glycerin 99% -USP | 38.7 |
| Dow Corning 5225C | 12 |
| Dow Corning 345 | 8 |
| 20% KOH | 0.04 |
| NEOLONE ™ | 0.1 |
| Water | 40.16 |

Example 3

An anti-itch gel including the ingredients listed below in Table 3 was prepared.

TABLE 3

| Ingredient | Weight Percent (w/w) |
|---|---|
| Pramoxine HCl - USP | 1 |
| Glycerin 99% - USP | 40.2 |
| Dow Corning 5225C | 10 |
| Dow Corning 345 | 7 |
| 12.5% KOH (0.005% solid KOH, 0.035% water) | 0.04 |
| NEOLONE ™ 950 | 0.1 |
| Water | 41.66 |

Example 4

Gel Preparation

The ingredients from Tables 1, 2, or 3 were combined to form a gel as follows. A first mixture was formed by combining the pramoxine, glycerin, NEOLONE™, and water to provide a water phase. The KOH was then added to reach a pH of about 5.0. A second mixture was formed by combining the Dow Corning 3225C and/or 5225C and the Dow Corning 345 to provide an oil phase. The refractive indices of the oil and water phases were measured and matched to within 0.001 using additional glycerin to increase the refractive index of the water phase or water to lower the refractive index of the oil phase. A small portion of the water phase was then added to the oil phase and mixed well at medium shear for about 10 minutes. The remainder of the water phase was then slowly added to the mixture over an approximately 30 minute period while increasing the shear of the mixing. When all of the water phase was added, the batch was mixed at high shear for about 2 minutes to give a substantially clear gel.

Example 5

Clinical Study

A test panel of 232 women was provided with a gel of the present invention and Vagisil® cream for comparison. When asked if the gel was less messy than the Vagisil® cream, 88% either agreed (28%) or strongly agreed (60%) that the gel was less messy than the cream. When asked if the gel left a residue, 91% either agreed (29%) or strongly agreed (62%) that the gel did not leave a residue, thus being transparent. From these results it was clear that women, by an approximately 80% margin, preferred the gels of the present invention.

Example 6

Rheology

Figure 3:
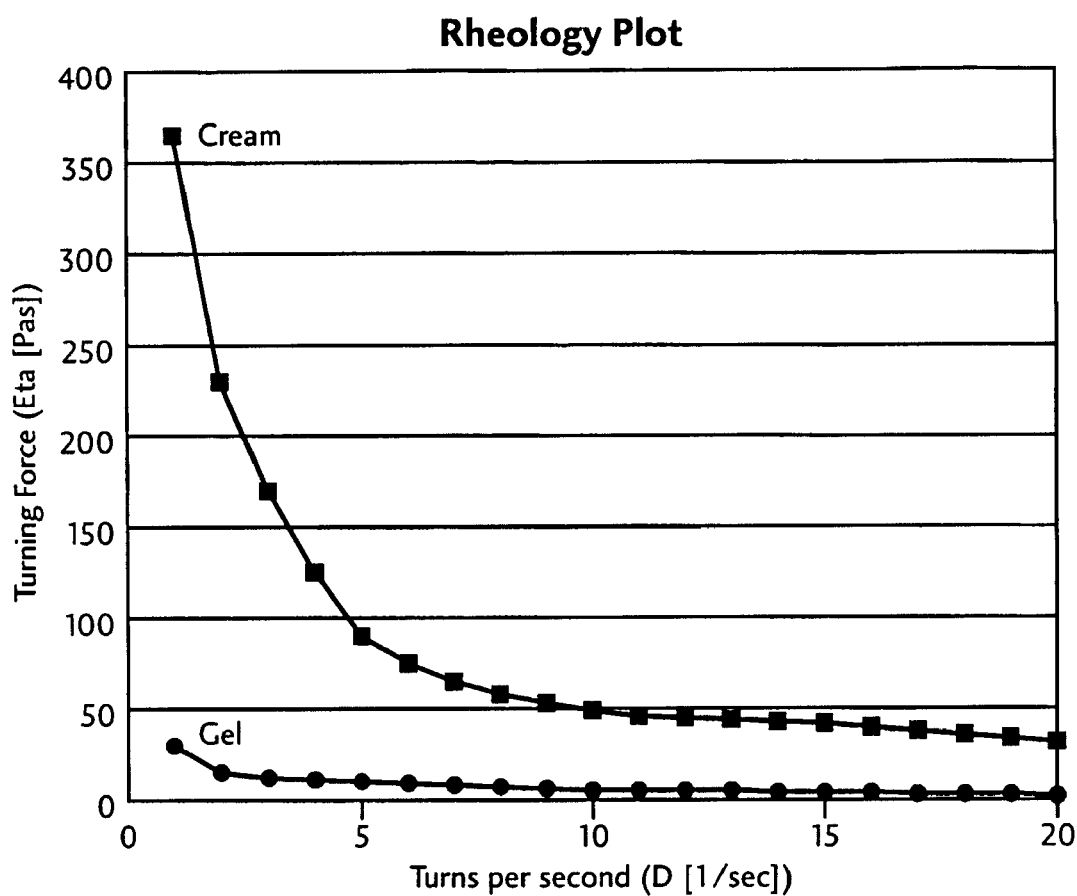
FIG. 3 is a rheology plot of a gel in accordance with the present invention and a conventional cream.

FIG. 3 is a rheology (low shear viscosity) plot of a gel in accordance with the present invention and Vagisil® cream. The measurements were collected on a Brookfield DV3+ rheometer having a 25 mm bob and cup at 30° C. The Y-axis of the graph shows the amount of force required to turn the cup, while the X-axis shows the number of turns per second. The figure establishes that the cream has an approximately 12-15× greater turning force between 1 and 5 seconds than a gel of the present invention.

Rheology turning force values, especially those obtained between 1 and 5 turns per second, relate to how "greasy" a preparation feels when applied to the skin, with higher turning force values signifying greasier feeling products. Thus, the gels of the present invention feel significantly less greasy during application than conventional creams. In one aspect, the anti-itch gels of the present invention have a turning force of at most 70 Eta[Pas], more preferably at most 50 Eta[Pas], between 0 and 5 turns per second.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An anti-itch gel, for treating itching of the vulvar tissues, comprising:
   20-60% by weight water,
   a water-soluble salt of pramoxine,
   a pH modifier,
   from 5 to 60% by weight of a protectant, and
   a water-in-oil emulsifier comprising one or more silicones, where the gel has a turbidity of less than 100 nephelometric turbidity units and the gel has a pH from 4 to 7, and
   the gel comprises colloidal particles having average particle diameters of from 1 to 50 microns.

2. The gel of claim 1 having a turbidity of less than 40 nephelometric turbidity units.

3. The gel of claim 1 having a turbidity of from 25 to 35 nephelometric turbidity units.

4. The gel of claim 1, where the gel comprises colloidal particles having average particle diameters of from 2 to 8 microns.

5. The gel of claim 1 having a turning force of at most 70 Eta[Pas] between 0 and 5 turns per second when measured on a rheometer.

6. The gel of claim 1 having a pH from 5 to 5.3.

7. The gel of claim 1, where water comprises from 37 to 42% of the gel by weight.

8. The gel of claim 1, where the water-in-oil emulsifier comprises at least one silicone.

9. The gel of claim 8, where the water-in-oil emulsifier comprises from 5 to 20% of the gel by weight.

10. The gel of claim 8, where the water-in-oil emulsifier comprises from 10 to 12% of the gel by weight.

11. The gel of claim 1, where the water-in-oil emulsifier comprises a dimethicone copolyol based emulsifier.

12. The gel of claim 11, where the dimethicone copolyol based emulsifier comprises a cyclopentasiloxane and a non-volatile dimethicone.

13. The gel of claim 1 comprising less than 10% by weight of a substantially water-soluble surfactant.

14. The gel of claim 1, further comprising from 0.01 to 1% by weight of a preservative.

15. The gel of claim 1, further comprising from 2 to 20% by weight of a silicone-based emollient.

16. The gel of claim 15, where the silicone-based emollient comprises a cyclomethicone.

17. The gel of claim 1, where the water-soluble anesthetic comprises from 0.5 to 2% by weight of a salt of pramoxine.

18. The gel of claim 1, where the water-soluble anesthetic comprises from 0.9 to 1.1% by weight of a salt of pramoxine.

19. The gel of claim 1, where the pH modifier comprises from 0.005 to 0.08% by weight of the gel and comprises a base.

20. The gel of claim 1, where the protectant comprises glycerin.

21. The gel of claim 20, where the protectant comprises from 20 to 45% by weight of the gel.

22. The gel of claim 1, where the protectant comprises dimethicone and comprises from 5 to 30% by weight of the gel.

23. The gel of claim 1, further comprising at least one odor modifier.

24. A method for treating vulvar discomfort, comprising: contacting vulvar tissue with the anti-itch gel of claim 1.

25. A method of forming the anti-itch gel of claim 1, comprising:
combining a water phase with an oil phase after matching the refractive indices of the water and oil phases to within 0.0004 to 0.0017 to provide the gel a turbidity of less than 100 nephelometric turbidity units; where
the water phase comprises the water, the water-soluble anesthetic, and the protectant; and
the oil phase comprises the water-in-oil emulsifier.

26. The method of claim 25, where the gel comprises colloidal particles having average particle diameters of from 2 to 8 microns.

27. The method of claim 25, where the gel has a pH from 5 to 5.3.

28. The method of claim 25, where the water-in-oil emulsifier comprises from 5 to 20% of the gel by weight and comprises a dimethicone copolyol based emulsifier.

29. The method of claim 28, where the dimethicone copolyol based emulsifier comprises a cyclopentasiloxane and a non-volatile dimethicone.

30. The method of claim 25, where the oil phase further comprises a silicone-based emollient comprising a cyclomethicone.

31. The method of claim 25, where the protectant comprises glycerin.

32. The gel of claim 1, comprising:
0.5 to 2% by weight of the water-soluble salt of pramoxine,
the pH modifier,
20 to 45% by weight of the protectant,
5 to 20% by weight of the water-in-oil emulsifier,
where the gel has a turbidity of less than 40 nephelometric turbidity units, and a pH from 5 to 5.3.

* * * * *